(12) United States Patent
Jung et al.

(10) Patent No.: US 6,485,743 B1
(45) Date of Patent: Nov. 26, 2002

(54) METHOD AND COMPOSITION OF AN ORAL PREPARATION OF ITRACONAZOLE

(75) Inventors: Jae-Young Jung, Kyunggi-do (KR); Kye-Hyun Kim, Kyunggi-do (KR); Sang-Heon Lee, Kyunggi-do (KR); Ji-Woong Hong, Kyunggi-do (KR); Jong-Woo Park, Kyunggi-do (KR); Kyu-Hyun Lee, Kyunggi-do (KR)

(73) Assignee: Choongwae Pharma Corporation, Seoul (KR)

( * ) Notice: Subject to any disclaimer, the term of this patent is extended or adjusted under 35 U.S.C. 154(b) by 0 days.

(21) Appl. No.: 09/582,536

(22) PCT Filed: Dec. 17, 1998

(86) PCT No.: PCT/KR98/00436

§ 371 (c)(1), (2), (4) Date: Jun. 29, 2000

(87) PCT Pub. No.: WO99/33467

PCT Pub. Date: Jul. 8, 1999

(30) Foreign Application Priority Data

Dec. 31, 1997 (KR) .............................. 97-81947
Jul. 10, 1998 (KR) .............................. 98-27730

(51) Int. Cl.[7] .............................. A61K 9/20; A61K 9/48; A61K 9/14
(52) U.S. Cl. .................. 424/464; 424/451; 424/455; 424/456; 424/469; 424/458; 424/489
(58) Field of Search .................. 424/464, 469, 424/451, 455, 456, 458, 489

(56) References Cited

U.S. PATENT DOCUMENTS

| 4,267,179 A | 5/1981 | Heeres et al. |
| 4,764,604 A | 8/1988 | Muller |
| 5,776,495 A | 7/1998 | Duclos et al. |

FOREIGN PATENT DOCUMENTS

| EP | 0 063 014 | 10/1982 |
| EP | 0 277 042 A2 | 8/1988 |
| EP | 0 570 606 A1 | 11/1993 |
| FR | 2 722 984 A1 | 2/1996 |
| JP | 1-100116 | 4/1989 |
| WO | WO 85/02767 | 7/1985 |
| WO | WO 90/11754 | 10/1990 |
| WO | WO 93/15719 | 8/1993 |
| WO | WO 9405263 | * 3/1994 ............ A61K/9/16 |
| WO | WO 95/31178 | 11/1995 |
| WO | WO 96/39835 | 12/1996 |
| WO | WO 97/44014 | 11/1997 |

OTHER PUBLICATIONS

J. Heykants et al., "The Clinical Pharmacokinetics of Itraconazole: An Overview", Mycoses (Suppl. 1), pp. 67–87, 1989.
M. J. Arias et al., "Influence of the Preparation Method of Solid Dispersions on their Dissolution Rate: Study of Triamterene–D–Mannitol System", International Journal of Pharmaceutics, vol. 123, pp. 25–31, 1995.
J. M. Gines et al., "Thermal Investigation of Crystallization of Polyethylene Glycols in Solid Dispersions Containing Oxazepam", International Journal of Pharmaceutics, vol. 143, pp. 247–253, 1996.
Albert S. Kearney et al., "Effect of Polyvinylpyrrolidone on the Crystallinity and Dissolution Rate of Solid Dispersions of the Anti–inflammatory CI–987", International Journal of Pharmaceutics, vol. 104, pp. 169–174, 1994.
V. Tantishaiyakul et al., "Properties of Solid Dispersions of Piroxicam in Polyvinylpyrrolidone K–30", International Journal of Pharmaceutics, vol. 143, pp. 59–66, 1996.
Hideshi Suzuki et al., Solid Dispersions of Benidipine Hydrochloride. I. Preparations Using Different Solvent Systems and Dissolution Properties, Chem. Pharm. Bull., vol. 44(2), pp. 364–371, 1996.

* cited by examiner

Primary Examiner—Thurman K. Page
Assistant Examiner—Robert M. Joynes
(74) Attorney, Agent, or Firm—Richard D. Schmidt; Venable

(57) ABSTRACT

The present invention relates to a method and composition of an oral preparation of itraconazole, an excellent azole antifungal drug. More particularly, it relates to an oral preparation of itraconazole having improved bioavailability, which is prepared by following steps of: i) dissolving itraconazole and hydrophilic polymer with solvent, ii) spray-drying said mixture, and iii) preparing the solid dispersions for oral preparation. The solid dispersions prepared in this invention may be useful in preparing tablets, granules and other oral dosage forms.

4 Claims, No Drawings

METHOD AND COMPOSITION OF AN ORAL PREPARATION OF ITRACONAZOLE

TECHNICAL FIELD

The present invention relates to a method and composition of an oral preparation of itraconazole, an excellent azole antifungal drug. More particularly, it relates to a method and composition of an oral preparation of itraconazole having improved bioavailability, which is prepared by following steps of: i) dissolving itraconazole and hydrophilic polymer with solvent, ii) spray-drying said mixture, and iii) preparing the solid dispersions for oral preparation.

In other words, the present invention relates to an oral preparation of itraconazole, which has improved bioavailability by enhancing water solubility and rapidly being dissoluble regardless of food intake, prepared using a solid dispersions having itraconazole and pH-dependent, pharmaceutically safe, fastly dissolved at a low pH and hydrophilic polymer with the steps of i) dissolving and ii) spray-drying for the formation of an oral preparation of itraconazole having water-insoluble property.

BACKGROUND ART

Itraconazole or (±)-cis-4-[4-[4-[4-[[2-(2,4-dichlorophenyl)-2-(1H-1,2,4-triazol-1-ylmethyl)-1,3-dioxolan-4-yll]methoxy]phenyl]-1-piperazinyl]phenyl]-2,4-dihydro-2-(1-methylpropyl)-3H-1,2,4-triazol-3-one, is a broadspectrum antifungal compound, and has been considered as an efficacious and safe drug.

Itraconazole has been developed as a broad antifungal agent for oral, parenteral and topical use and is disclosed in U.S. Pat. No. 4,267,179, but usually has been administered in oral route. Further, itraconazole is efficacious in oral administration, because it has a tendency of extensive tissue distribution [*Mycoses* 32 (Suppl. 1), p67~87, 19891].

It has been reported that itraconazole has a pH-dependent solubility characterized in the ionization only at a low pH, such as, a gastric juice, and many attempts have been carried out to increase solubility and bioavailability, because itraconazole is almost insoluble in water (less than $1 \mu g/ml$) and in diluted acidic solution(less than $5 \mu g/ml$).

Generally, it has been reported that water insoluble drug has low dissolution property from the solid preparation. For increasing the solubility and dissolution rate of poorly water-soluble drugs, extensive studies of solubilization have shown that a wide variety of type of drugs can be efficiently solubilized by surfactants, hydrophilic carriers or pro-drugs, etc. Among them, a solid dispersion of drug and inert hydrophilic polymer has been suggested to enhance the solubility of insoluble drug. Further, many researches have been reported to enhance the solubility, dissolution rate and bioavailability of insoluble drug by preparing a solid dispersion of insoluble drug and inert carrier [①*International Journal of Pharmaceutics*, Vol. 104, p169~174(1994), ②*International Journal of Pharmaceutics*, Vol. 143, p247~253(1996)].

The term "a solid dispersion" defines a system in a solid state comprising at least two components, wherein one component is dispersed more or less evenly throughout the other component or components. Many factors have been known to affect the solubility of a solid dispersion.

Prior references related to oral preparation for increasing bioavailability of itraconazole are as follows:

1) The solubility and bioavailability of a drug are increased by complex using cyclodextrin or its derivative in WO 85/02767 and U.S. Pat. No. 4,764,604, 2) The aerosol preparation is prepared by reducing the particle size of a drug in WO 90/11754, 3) The liposomal preparation for external use including itraconazole is prepared containing phospholipid and by solvent system in WO 93/15719, 4) The preparation for external use adhering to the nasal mucous membrane or the vaginal mucous membrane is prepared by emulsion or aqueous solution using cyclodextrin or its derivative in WO 95/31178, 5) The oral preparation to increase solubility and bioavailability of drug is disclosed in WO 94/05263, in which hydrophilic polymer such as hydroxypropyl methylcellulose is coated with about 25–30 mesh sugar spheres, and such preparation of itraconazole is commercially marketed as the trademark "SPORANOX", 6) The solid dispersions comprising drug and hydrophilic polymer according to the melt-extrusion method is disclosed in WO 97/44014, in which bioavailability is improved by increasing dissolution rate of drug and food effect is minimized according to the food intake.

Generally, there is a solvent method, a melting method or a solvent-melting method, etc. for preparing solid dispersions using hydrophilic polymer as carrier. In the solvent methods, a freezing drying method, a drying method or a nitrogen-gas drying method has not a few drawbacks, low reproducibility of preparation, the higher cost of preparation and long time in the preparation, etc. In the melting method, the careful attention of working process is demanded because raising temperature over melting point affects the stability of drug and cooling condition of melting mixture also affects the property of preparation. Further, even though a solvent-melting method is carried out when a solvent method or a melting method cannot be used alone, it has not a few drawbacks, for example, a lot of manipulation steps and time.

However, the spray-drying method used in this invention has some advantages, for example, short preparation time and maintaining low temperature, because the drug and the carrier dissolved in a solvent are immediately dried after spraying. Therefore, because the stability of drug is not affected by raising temperature, the spray-drying method is efficient in industrialization.

A disclosed preparation of WO 94/05263 is concerned with the beads comprising a 25~30 mesh core, a coating film of a hydrophilic polymer and an antifungal agent, and a seal coating layer, and materials suitable for use in a fluidized bed granulator(Glatt™) with a Wurster bottom spray insert. A seal coating polymer layer is applied to the drug coated cores to prevent sticking of the beads which would have the undesirable effect of a concomitant decrease of the dissolution rate and of the bioavailability.

However, the reason why sugar sphere having appropriate dimensions(about 25–30 mesh) has to be used is to minimize the tendency toward agglomeration among sugar spheres in the drug coating process. In addition, during the preservation of the prepared beads filled in hard-gelatin capsules, sticking of the beads results in the undesirable decrease of the bioavailability. Therefore, a seal coating polymer layer has to be applied to the drug coated cores to prevent sticking of the beads. This is undesirable for demanding unnecessary step in the preparation.

On the other hand, the spraying rate in the preparation manufactured by said patent is regulated carefully to prevent undesirable drying or moisturization. Further, spraying air pressure is controlled to prevent formation of big bead and increasing of agglomeration during the coating process. Also, there is some drawbacks of spending the long time in drying, because fluidizing air volume has to be monitered carefully and inlet-air temperature has to be controlled.

The influence of food and dose on the oral bioavailability of itraconazole was studied. The relative systematic availability of itraconazole (PEG capsules) compared with solution averaged 40% in the fasting state but 102%(1.92 μg h/ml) in the post-prandial state. Food did not significantly affect the rate of absorption of the capsules. Areas under the curve at single doses of 50, 100 and 200 mg had a ratio of 0.3:1:3, suggesting non-linear itraconazole pharmacokinetics in the range of therapeutically used doses. It was also concluded from the study that to ensure optimal oral absorption, itraconazole may be administered either in capsules shortly after a meal or in solution, the absorption of which is not influenced by the presence of food in the stomach [Mycoses 32 (Suppl. 1), p67~87, 1989].

Meanwhile, the solid dispersions using the melt-extrusion method in WO 97/44014 is prepared by following steps: i) mixing the itraconazole and pharmaceutically acceptable hydrophilic polymer, ii) optionally blending additives with the thus obtained mixture, iii) heating the thus obtained blend until one obtains a homogenous melt, iv) forcing the thus obtained melt through one or more nozzles, v) cooling the till it solidifides. Obtained solid dispersions is characterized in increasing dissolution rate of drug and lowering food effect, that is, bioavailability change of drug dependent upon the food intake.

The melting temperature and melting time of polymer and drug are important factors in the solid dispersions preparation by the melt-extrusion method disclosed prior reference. In this reference, it was reported that dissolution rate of solid dispersions is decreased at a low temperature, because drug and polymer are not melted sufficiently, and that polymer cannot be used at a higher temperature owing to decomposition of polymer. Therefore, setting of melting temperature is very important. Further, to perform the cited method, extra equipment for preparing melt-extrusion and special technique to handle this equipment have to be required.

Particularly, hydrophilic polymers, such as, cellulose derivatives such as hydroxypropyl methylcellulose; natural gum such as tragacanth gum; polyvinylacetal diethylaminoacetate (trademark "AEA"); and polymethacrylic acid and its copolymer become char phase due to the decomposition of polymers on condition that melting time is long at relatively low temperature. The charred solid dispersions results in a serious problem of dissolution rate and stability of preparation due to the change of original character of polymer.

Also, the solid dispersions disclosed in prior reference is prepared by melt-extrusion and grinding to particles having the particle size less than 600 μm in the Fitzmill twice. Then, yield of preparation is relatively low as 78%. Further, there are some drawbacks of long preparation step by adding the grinding process.

The present invention has developed the oral preparation of itraconazole having improved bioavailability prepared by preparing the solid dispersions. In this invention, the problems of prior method is solved by increasing pharmaceutical stability of heating, shortening of the manufacturing time and enhancing the yield of preparation using the spray-drying method in the solvent methods. Then, organic solvent is no longer remained in this method.

Also, the present invention developed the solid dispersions having itraconazole and pH-dependent, pharmaceutically safe, fastly dissolved at a low pH and hydrophilic polymer with the steps of i) dissolving and ii) spray-drying for the formation of an oral preparation of itraconazole having water-insoluble property. Further, the bioavailability of drug is improved and the food effect, that is, bioavailability change of drug dependent upon the food intake is minimized by increasing dissolution rate considerably in itraconazole preparation.

DISCLOSURE OF INVENTION

The object of the present invention is to provide an oral preparation of itraconazole having improved bioavailability, which is prepared by following steps of: i) dissolving 1 wt parts of itraconazole and 0.5~5.0 wt parts of pH-dependent inert hydrophilic polymer with at least one solvent selected from the group consisting of methylenechloride, chloroform, ethanol and methanol, ii) dispersing and spray-drying said mixture, and iii) preparing the solid dispersions for oral preparation.

Also, said pH-dependent inert hydrophilic polymer is at least one polymer selected from the group consisting of polyvinylacetal diethylaminoacetate and aminoalkyl methacrylate copolymer. And, said oral preparation of itraconazole is prepared by following compositions comprising 1.0~2.5 wt parts of said polymer as to 1 wt parts of itraconazole. Further, the concentration of solution dissolving itraconazole and pH-dependent inert hydrophilic polymer is 3~10% (w/w), and inlet temperature is 30~60° C. at spray-drying.

BEST MODE FOR CARRYING OUT THE INVENTION

Itraconazole has a weak basic property with pKa 3.7 and is ionized in acidic environment such as in the stomach. It has lipophilic property in nature, with oil/water partition coefficient being 5.66 in the pH 8.1 aqueous buffer/n-octanol system.

AEA™ and Eudragit™ E are hydrophilic polymers possessing the characteristic tertiary amine functional groups and are frequently used in protective or gastric soluble coating. Unlike other hydrophilic polymers, for example, Hydroxypropyl methylcellulose 2910, Methylcellulose, Hydroxyethylcellulose, Hydroxypropylcellulose, Sodium carboxymethylcellulose, etc. which release drug upon swelling, AEA™ and Eudragit™ E are solubilized under pH 5 in a pH-dependent manner, for increasing the dissolution profile of poorly water soluble drugs. The absorption of dissolved itraconazole from the stomach is not a problem in itself.

The pH-dependent hydrophilic polymer used in this invention, for example, polyvinylacetal diethylaminoacetate (trademark "AEA") or aminoalkyl methacrylate copolymer (trademark "Eudragit E") is dissolved in acid solution only at a pH in the range of 1~5. Further, 0.5~5.0 wt parts of said pH-dependent hydrophilic polymer, preferably, in the range of 1.0~2.5 wt parts of the polymer is contained as to 1 wt parts of insoluble drug. In case that the content of polymer is less than 0.5 wt parts, the solubility of drug with carrier shall decrease, because a solid dispersions is not formed completely, and such fact is confirmed by observing endothermic peak by melting of drug in Differential Scanning Calorimetry. In case that the content of polymer is more than 5.0 wt parts, initial dissolution rate shall decrease by polymer, and patient adaptability can be reduced by big size of preparation in taking drug.

The oral preparation in this invention is prepared by preparing the solid dispersions, which can be mass-produced in a large amount using spray dryer. The organic solvent, such as, methylenechloride or chloroform is used for dissolving insoluble drug and hydrophilic polymer before spray-drying, and methanol or ethanol can be mixed to said solution. The amount of solvent for spray-drying shall be required in the concentration of hydrophilic polymer to be 3~10% (w/w), preferably, 5% (w/w). Also, inlet temperature of dissolved mixture is 30~60° C., preferably, 35~45° C., and inlet amount of dissolved mixture can be changed properly according to the concentration of polymer. The yield of solid dispersions may be more than 95%.

Also, the solid dispersions used in this invention can be manufactured as not only tablet but form of oral preparation, such as, powder, granule, granule capsule, pellet capsule by the known method. Therefore, there are many choices in preparation development.

The diluent can be added to solid dispersions in order to manufacture oral preparation in this invention. For example, lactose, starch, sodium starch glycolate (Explotab™), crospovidone (Kollidone CL™, Kollidone CL-M™), cros-carmellose sodium (AC-Di-Sol™) or maltodextrin (Maltrine™) is used as a disintegrant in preparation. Further, stearic acid, magnesium stearate or talc is used as a lubricant.

The present invention will be more specifically explained by the following examples. However, it should be understood that the examples are intended to illustrate but not in any manner to limit the scope of the present invention.

EXAMPLES 1~7

Preparation of the Solid Dispersions by the Spray-drying Method

The solution for spray-drying is manufactured by following steps of:

i) dissolving polymer with methylenechloride as indicated Table 1., ii) adding 10 g of drug to said polymer to be dissolved, and iii) filtering the mixture using 10 μm filter. The concentration of hydrophilic polymer in solution is 5% (w/w). Buchi 190 mini spray dryer is used at spray-drying, inlet temperature is about 40° C. and the rate of spray is 10 ml/min.

Preparation of Itraconazole Tablet Using Solid Dispersion by Compaction Granulation A slug is prepared by constant pressing to the obtained solid dispersions, and the granule is prepared after grinding the slug. Obtained granule is sieved by passing the 35 mesh, and sieved granule is mixed with microcrystalline cellulose and pregelatinized starch (0.75:0.25) in the weight ratio of 1:1. Kollidon™ CL is mixed as disintegrant, magnesium stearate is mixed as lubricant, and Cab-O-Sil and talc are mixed as glidant. Finally, tablets are obtained by compressing said mixture.

Also, the capsule is filled with mixture of said granule and suitable diluent, and the pellet can be manufactured by powder layering method using said solid dispersions by rotor tangential spray coater.

TABLE 1

Composition of the oral preparation of itraconazole manufactured in examples 1~7

(unit: g)

| Material | Example 1 | 2 | 3 | 4 | 5 | 6 | 7 |
|---|---|---|---|---|---|---|---|
| Itraconazole | 20 | 20 | 20 | 20 | 20 | 20 | 20 |
| Eudragit ™ E | 10 | 20 | 30 | 40 | 10 | 5 | 0 |
| AEA ™ | 10 | 5 | 5 | 0 | 20 | 30 | 40 |
| Microcrystalline cellulose | 30 | 33.75 | 41.25 | 45 | 30 | 41.25 | 45 |
| Pregelatinized starch | 10 | 11.25 | 13.75 | 15 | 10 | 13.75 | 15 |
| Cab-O-Sil ™ | 1.2 | 1.35 | 1.65 | 1.8 | 1.2 | 1.65 | 1.8 |
| Talc | 1.2 | 1.35 | 1.65 | 1.8 | 1.2 | 1.65 | 1.8 |
| Kollidon ™-CL | 4 | 4.5 | 5.5 | 6 | 4 | 5.5 | 6 |
| Mg. stearate | 0.8 | 0.9 | 1.1 | 1.2 | 0.8 | 1.1 | 1.2 |

COMPARATIVE EXAMPLES 1~5

Preparation of the Solid Dispersions by the Spray-drying Method

The solution for spray-drying is manufactured by following steps of: i) dissolving polymer with methylenechloride as indicated Table. 2, ii) adding 10 g of drug to said polymer and to be dissolved, and iii) filtering the mixture using 10 μm filter. The concentration of hydrophilic polymer in solution is 5% (w/w). Buchi 190 mini spray dryer is used at spray-drying, inlet temperature is about 40° C. and the rate of spray is 10 ml/min.

Preparing the Preparation by the Spray-drying Method

The granule suitable for tabletting is manufactured by adding 10% of aqueous lactose solution to solid dispersions. The manufactured granule is converted into particle using 35 mesh sieve, and into particle using 35 mesh sieve after drying at 40° C. for 1 day. The tablet is manufactured by following steps of: i) mixing dried granule with 35 mesh-passed lactose at the ratio of 1:1 (w/w), ii) adding Explotab as disintegrant to said mixture, iii) adding magnesium stearate as lubricant to said mixture and to be lubricated, and iv,) tabletting the mixture.

TABLE 2

Composition of the oral preparation of itraconazole manufactured in comparative example 1~5

(unit: g)

| Material | Comparative example 1 | 2 | 3 | 4 | 5 |
|---|---|---|---|---|---|
| Itraconazole | 20 | 20 | 20 | 20 | 20 |
| Eudragit ™ L | 30 | — | — | — | — |
| Eudragit ™ S | — | 30 | — | — | — |
| Eudragit ™ RL | — | — | 30 | — | — |
| Eudragit ™ RS | — | — | — | 30 | — |
| Hydroxypropyl methylcellulose 2910 | — | — | — | — | 30 |
| Lactose | 50 | 50 | 50 | 50 | 50 |
| Explotab ™ | 5.0 | 5.0 | 5.0 | 5.0 | 5.0 |
| Magnesium stearate | 0.5 | 0.5 | 0.5 | 0.5 | 0.5 |

COMPARATIVE EXAMPLES 6~7

Preparation of the Solid Dispersions by the Melting Method

The solid dispersion is manufactured by following steps of: i) mixing polymer with drug at the ratio of 1:1.5 (w/w) using polymer as shown in Table 3., ii) agitating said mixture at 170° C., melting temperature of drug, to be melted, iii) cooling to room temperature, iv) grinding using hammer mill, and v) refining polymer using 35 mesh sieve.

Preparing the Preparation by the Melting Method

The preparation is manufactured as the same manners of the example.

TABLE 3

Composition of the oral preparation of itraconazole manufactured in comparative examples 6~7

|  | (unit: g) Comparative example | |
| --- | --- | --- |
| Material | 6 | 7 |
| Itraconazole | 20 | 20 |
| Eudragit ™ E | 30 | — |
| Hydroxypropylcellulose 2910 | — | 30 |
| Lactose | 50 | 50 |
| Explotab ™ | 5.0 | 5.0 |
| Magnesium stearate | 0.5 | 0.5 |

EXAMPLE 9

Comparative Test of Solubility of the Solid Dispersions in Polymer

This test is carried out by following steps of: i) laying itraconazole powder (equivalent to 25 mg of itraconazole) and the solid dispersions (itraconazole:hydrophilic polymer=1:1.5 (w/w)) to 20ml of test tube, ii) adding 10 ml of simulated gastric juice (pH 1.2) for dissolution test in U.S.P. XXIII general experimental protocol to said mixture, iii) ultrasonic treating said mixture for 30 minutes to have sufficient moisty, iv) agitating it at 100 rpm for 24 hours in shaking water bath (25° C.), v) centrifuging 5 ml of each sample at 4,000 rpm for 20 minutes, vi) filtering supernatant using 0.45μm membrane, vii) centrifuging said supernatant at 14,000 rpm for 10 minutes again, and vii) collecting supernatant and analyzing content of drug by HPLC and determining solubility. The experimental result is shown in Table 4.

TABLE 4

Comparative test of solubility of the solid dispersions in polymer

| Test sample | | | Solubility (μg/ml) |
| --- | --- | --- | --- |
| solid dispersion | pH-independent hydrophilic polymer | Polyethylene glycol 20,000 | 16.54 ± 2.69 |
| | | Poloxamer 188 | 11.93 ± 1.03 |
| | | Povidone K 25 | 63.83 ± 4.27 |
| | | Hydroxypropyl methylcellulose | 132.35 ± 8.14 |
| | pH-dependent hydrophilic polymer | Eudragit ™ E | 230.84 ± 2.58 |
| | | AEA ™ | 264.83 ± 0.60 |
| Itraconazole powder | | | 1.38 ± 0.11 |

Number of test sample = 3, Average ± Standard deviation

The solid dispersions of itraconazole and pH-dependent hydrophilic polymer, such as, AEA™ or Eudragit™ E has excellent solubility as compared with the solid dispersions of itraconazole and pH-independent hydrophilic polymer, such as, polyethylene glycol, poloxamer, povidone or hydroxypropyl methylcellulose, and the result is shown in Table. 5. The solubility of said solid dispersions is improved about 170~200 times as compared with drug powder in simulated gastric juice (pH 1.2).

EXAMPLE 10

Comparative Test of Dissolution of the Solid Dispersions in Polymer

The solid dispersions (itraconazole:hydrophilic polymer=1:1.5 (w/w)) manufactured using different polymers are tabletted. Then, dissolution test is carried out according to the dissolution test in U.S.P. XXIII general experimental protocol, and simulated gastric juice (pH 1.2±0.1) is used as test solution. One tablet (equivalent to 100 mg of itraconazole) is used and the amount of dissolved drug (% released) is measured in each time interval. The experimental result is shown in Table 5.

TABLE 5

Comparative test of dissolution of the solid dispersions in polymer

| Test sample | | Time Amount of dissolved medicine (% Released) | | | |
| --- | --- | --- | --- | --- | --- |
| | | 5 min | 10 min | 30 min | 60 min |
| solid dispersion | | | | | |
| pH-independent hydrophilic polymer | Poloxamer 188 | 6.82 ± 0.25 | 8.35 ± 0.14 | 8.57 ± 0.24 | 9.71 ± 0.64 |
| | Hydroxypropyl methylcellulose | 7.16 ± 0.78 | 19.55 ± 1.44 | 48.90 ± 1.30 | 64.87 ± 1.25 |
| | Povidone K 25 | 4.07 ± 1.06 | 8.45 ± 1.44 | 23.09 ± 1.40 | 33.69 ± 1.30 |
| pH-dependent hydrophilic polymer | AEA ™ | 94.07 ± 2.63 | 98.64 ± 4.12 | 100.86 ± 2.51 | 100.00 ± 1.45 |
| | Eudragit ™ E | 95.08 ± 2.39 | 98.96 ± 4.45 | 99.87 ± 4.13 | 99.94 ± 4.51 |

Number of test sample = 3, Average ± standard deviation

The solid dispersions of itraconazole and pH-dependent hydrophilic polymer, such as, AEA™ or Eudragit™ E has excellent dissolution rate, and the result is shown in Table 5.

EXAMPLE 11

Differential Scanning Calorimetry of Itraconazole Powder and Solid Dispersions

Differential Scanning Calorimetry (DSC) is carried out by following steps of: i) laying the solid dispersions (equivalent to about 5 mg of itraconazole) of example 9 and itraconazole powder to aluminum melting pot, ii) purging nitrogen gas at 20 ml/min, and iii) raising temperature at 10° C./min, and the solid dispersions is obtained.

NETZSCH DSC-200 (Germany) is used as differential scanning calorimeter. The solid dispersions of itraconazole and polymer, such as, polyethylene glycol(PEG) 20,000 or poloxamer 188 shows endothermic peak near 166° C. by melting of itraconazole, but the solid dispersions of itraconazole and polymer, such as, povidone (Kollidone™ 25), hydroxypropyl methylcellulose (HPMC), Eudragit™ E or AEA™ doesn't.

Differential Scanning Calorimetry (DSC) is carried out after manufacturing solid dispersions, in which the weight-by-weight ratio of drug :pH-dependent hydrophilic polymer, such as, AEA™ or Eudragit™ E is from 1:0.5 to 1:2.

The endothermic peak of drug has a tendency to decrease according to increasing the content of pH-dependent hydrophilic polymer (AEA™, Eudragit™ E), and solid dispersions having more than 1:1 of the weight-by-weight ratio of drug (itraconazole):hydrophilic polymer (AEA™, Eudragit™ E) doesn't show endothermic peak by melting of drug. Therefore, it is concluded that solid dispersions is formed at more than 1:1 of the weight-by-weight ratio of drug (itraconazole): hydrophilic polymer (AEA™, Eudragit™ E).

Differential Scanning Calorimetry (DSC) is carried out by using solid dispersions of itraconazole and piroxicam or benedipine hydrochloride. Single drug shows endothermic peak by melting of drug clearly, but solid dispersions doesn't. This results are disclosed in references [①*International Journal of Pharmaceutics*, Vol. 143, p59~66(1996), ②*Chemical Pharmaceutical Bulletin*, Vol. 44, No. 2, p364~371(1996)].

Also, to compare physical mixture of itraconazole and pH-dependent hydrophilic polymer (AEA™, Eudragit™ E) with solid dispersions of this invention, Differential Scanning Calorimetry (DSC) is carried out. The physical mixtures having 1:1 and 1:2 of the weight-by-weight ratio of drug (itraconazole):hydrophilic polymer (AEA™, Eudragit™ E) show endothermic peak by melting of drug clearly.

EXAMPLE 12

Powder X-ray Diffraction Test of Solid Dispersions of Itraconazole Powder and Polymer (AEA™ M, Eudragit™ E)

Powder X-ray diffraction test is carried out in solid dispersions of itraconazole powder and polymer (AEA™, Eudragit™ E). Enraf noinus FR 590 is used as instrument. The angle of diffraction according to the crystalline form of sample shows characteristic peak according to emitting X-ray at regular rate in Powder X-ray diffraction. Itraconazole shows characteristic peak of crystalline form, but solid dispersions doesn't. The crystalline form of itraconazole is transformed into amorphous form in solid dispersions. Therefore, it is concluded that solubility and initial dissolution rate is improved according to transformation of crystalline form into high energy amorphous form in preparation of solid dispersions, and this results are disclosed in reference (*International Journal of Pharmaceutics*, Vol. 123, p25~31(1995)).

Also, to compare physical mixture of itraconazole and pH-dependent hydrophilic polymer (AEA™, Eudragit™ E) with solid dispersions of this invention, Powder X-ray diffraction test is carried out. The physical mixture having 1:1.5 of the weight-by-weight ratio of drug (itraconazole) :hydrophilic polymer (AEA™, Eudragit™ E) shows characteristic peak of crystalline form.

EXAMPLE 13

Scanning Electron Microscopy Test of Solid Dispersions of Itraconazole Powder and Polymer (AEA™, Eudragit™ E)

Scanning electron microscopy test is carried out in solid dispersions of itraconazole powder and polymer (AEA™, Eudragit™ F.). JEOL, JSM-35CF is used as instrument. The surface and particle size of sample is confirmed by observing at magnification of high power in Scanning electron microscopy. Itraconazole powder shows several tens $\mu$m of particle distribution of crystalline form, but solid dispersions shows 1~5 $\mu$m of particle distribution of globular amorphous form. Therefore, it is concluded that solubility and initial dissolution rate is improved according to contacting with hydrophilic carrier closely due to small particle distribution in preparing solid dispersions, and this result is disclosed in reference (*International Journal of Pharmaceutics*, Vol. 123, p25~31(1995)).

EXAMPLE 14

Dissolution Test

The effect of a drug is measured in vitro according to the dissolution test in U.S.P. XXIII general experimental protocol. One tablet (equivalent to 100 mg of itraconazole) is used as preparation for dissolution test. The tablet is manufactured by Paddle method, in which revolving speed of Paddle is 100 rpm, temperature of dissolved solution is 37±0.5° C., and simulated gastric juice (pH 1.2±0.1) is used as test solution. 2 ml of dissolved solution is collected at 5, 10, 30, 60 minutes, and 2ml of simulated gastric juice (37° C.) is added to dissolved solution in each time. The amount of dissolved drug (% released) is measured by following steps of: i) centrifuging test sample, ii) filtering supernatant using 0.45$\mu$m membrane, and iii) analyzing content of drug by HPLC. Table 6. shows experimental result.

TABLE 6

| | Amount of dissolved medicine (% Released) (Number of test sample = 6, Average ± Standard deviation) Time | | | |
|---|---|---|---|---|
| Example | 5 min | 10 min | 30 min | 60 min |
| Example 1 | 94.58 ± 1.97 | 98.06 ± 1.76 | 98.25 ± 2.61 | 100.25 ± 0.74 |
| Example 2 | 95.07 ± 2.44 | 98.28 ± 0.78 | 99.86 ± 1.68 | 99.51 ± 1.01 |
| Example 3 | 93.08 ± 2.39 | 97.96 ± 4.45 | 100.47 ± 4.13 | 100.84 ± 4.51 |
| Example 4 | 96.87 ± 3.53 | 98.93 ± 1.61 | 99.80 ± 2.74 | 100.32 ± 2.32 |
| Example 5 | 95.48 ± 5.61 | 98.57 ± 1.79 | 99.98 ± 1.60 | 99.17 ± 1.75 |
| Example 6 | 94.91 ± 5.98 | 98.61 ± 2.93 | 100.47 ± 1.29 | 100.81 ± 2.16 |

TABLE 6-continued

Amount of dissolved medicine (% Released)
(Number of test sample = 6, Average ± Standard deviation)
Time

| Example | 5 min | 10 min | 30 min | 60 min |
|---|---|---|---|---|
| Example 7 | 94.50 ± 9.69 | 99.28 ± 2.49 | 100.87 ± 0.94 | 100.59 ± 1.31 |
| Comparative example 1 | 0 | 0 | 0.58 ± 0.01 | 0.61 ± 0.03 |
| Comparative example 2 | 0 | 0 | 0.78 ± 0.02 | 0.89 ± 0.01 |
| Comparative example 3 | 3.20 ± 0.78 | 6.89 ± 0.13 | 9.46 ± 0.74 | 11.25 ± 0.94 |
| Comparative example 4 | 3.10 ± 0.23 | 4.74 ± 0.47 | 7.48 ± 0.25 | 9.92 ± 0.32 |
| Comparative example 5 | 40.06 ± 0.78 | 59.55 ± 1.23 | 78.10 ± 1.20 | 89.87 ± 1.25 |
| Comparative example 6 | 39.91 ± 5.90 | 57.61 ± 2.93 | 60.47 ± 1.20 | 62.81 ± 2.10 |
| Comparative example 7 | 44.50 ± 9.60 | 50.25 ± 2.49 | 62.28 ± 2.49 | 72.59 ± 1.31 |
| Comparative example | 1.92 ± 0.42 | 17.60 ± 1.73 | 62.95 ± 2.57 | 86.46 ± 1.80 |

Comparative example: Capsule preparation (equivalent to 100 mg of itraconazole) (trademark SPORANOX)

The oral preparation manufactured by using solid dispersions (example 1~7) of this invention is dissolved very fastly and completely as compared with solid dispersions of comparative example in simulated gastric juice (pH 1.2), and the result is shown in Table 6.

EXAMPLE 15

Stability Test

Stability of preparation is confirmed by observing the change of dissolution rate of preparation according to laying samples at 40° C. and 75% of relative humidity for 2 months. Table 7. shows experimental result.

TABLE 7

Amount of dissolved medicine (%) (time: 30 min)

| Example | initial | 1 week | 2 week | 4 week | 8 week |
|---|---|---|---|---|---|
| Example 1 | 95.28 ± 2.61 | 94.25 ± 1.68 | 95.34 ± 1.74 | 93.47 ± 2.10 | 94.35 ± 1.34 |
| Example 3 | 97.84 ± 4.51 | 96.80 ± 4.50 | 95.74 ± 4.31 | 95.30 ± 4.21 | 95.85 ± 3.51 |
| Example 6 | 99.81 ± 2.16 | 98.80 ± 2.10 | 97.86 ± 2.11 | 96.51 ± 2.10 | 94.61 ± 2.14 |
| Comparative example 6 | 62.81 ± 1.20 | 62.75 ± 2.11 | 59.71 ± 2.30 | 55.51 ± 2.11 | 50.51 ± 1.90 |
| Comparative example 7 | 62.27 ± 1.31 | 57.50 ± 1.29 | 55.51 ± 1.30 | 51.54 ± 1.29 | 46.69 ± 1.24 |

REFERENCE EXAMPLE 1

Physical Stability Test of Hydrophilic Polymer in Melting

To confirm the thermostability of hydrophilic polymer in melting, phase change is observed apparently by laying polymers at the oven of 200° C. for 5 minutes after adding hydrophilic polymer in glass mortar respectively. Physical stability of polymer in heating is determined by measuring ΔE before and after heating using Chroma Meter (CR-200, Minolta, Japan).

After laying hydrophilic polymers at the oven of 200° C. for 5 minutes, the color of polymers is changed apparently, and a part of polymer is charred by being decomposed, and the result is shown in Table 8. The ΔE value measured by Chroma Meter is 30~70. Therefore, it is suggested that polymer is decomposed or its property is changed by heating.

TABLE 8

Experimental data of thermostability of polymer

| Polymer | Color | ΔE |
|---|---|---|
| Methylcellulose | pale brown | 50.52 |
| Hydroxyethylcellulose | black, light charred | 58.31 |
| Hydroxypropylcellulose | light black | 51.56 |
| Hydroxypropyl methylcellulose 2910 | black, light charred | 60.45 |
| Sodium carboxymethylcellulose | brown | 56.48 |
| Starch | pale yellow | 34.53 |
| Pectin | black, charred | 44.83 |
| Tragacanth | brown, light charred | 55.77 |
| Sodium alginate | black, light charred | 57.34 |
| Xanthan gum | black, charred | 69.48 |
| Carbopol 940 | pale yellow | 35.85 |
| Polyvinylalcohol (M.W.78,000) | brown | 49.15 |
| Polyvinylpyrrolidine K-30 | yellow | 60.52 |
| Polyethylene glycol 20,000 | light black | 53.35 |
| Poloxamer 407 | pale brown | 47.28 |
| AEA ™ | brown | 52.56 |
| Eudragit ™ E | pale brown | 32.40 |
| Eudragit ™ L | black | 60.01 |
| Eudragit ™ RL | brown | 61.80 |
| Eudragit ™ RS | pale brown | 53.64 |
| Eudragit ™ S | light black | 56.62 |

What is claimed is:

1. An oral preparation of itraconazole having improved bioavailability, which is prepared by dissolving 1.0 to 2.5 wt parts of at least one pH-dependent inert hydrophilic polymer selected from the group consisting of polyvinylacetal dithylarmoacetate and aminoalkyl methacrylate copolymer with 1.0 wt part of itraconazole in at least one solvent selected from the group consisting of methylenechloride, chloroform ethanol and methanol, and subjecting the resulting solution obtained after the dissolution to a dispersing and spray-drying process, to prepare particles of a solid dispersion consisting of itraconazole and said hydrophilic polymer for the manufacture of an oral preparation.

2. The oral preparation of itraconazole according to claim 1, wherein the pH-dependent inert hydrophilic polymer is dissolved in the solution in an amount of 1.0 to 2.0 wt parts, based on 1 wt part of said itraconazole.

3. The oral preparation of itraconazole according to claim 1, wherein the itraconazole and pH-dependent inert hydrophilic polymer are dissolved in the solution in a total concentration of 3 to 10% (w/w), and the spray-drying process is carried out at an inlet temperature of 35 to 40° C.

4. The oral preparation of itraconazole according to claim 1, wherein the sold dispersion is further prepared as a tablet, powder, granule or capsule.

* * * * *